United States Patent
Fabrizio (12) Patent No.: US 6,345,197 B1
(45) Date of Patent: *Feb. 5, 2002

(54) AGE-BASED HEART RATE TARGET ZONE METHOD AND APPARATUS

(75) Inventor: Robert A. Fabrizio, Norwalk, CT (US)

(73) Assignee: Acumen, Inc., Sterling, VA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/665,171

(22) Filed: Sep. 19, 2000

Related U.S. Application Data (63) Continuation of application No. 08/595,282, filed on Feb. 1, 1996, now Pat. No. 6,163,718.

(51) Int. Cl.$^7$ .......................................... A61B 5/0404
(52) U.S. Cl. ..................................................... 600/519
(58) Field of Search .................................. 600/519, 520, 600/522, 523

(56) References Cited

U.S. PATENT DOCUMENTS

| | | | | |
|---|---|---|---|---|
| 4,788,983 A | * | 12/1988 | Brink et al. ................ | 128/706 |
| 5,301,154 A | * | 4/1994 | Suga | |
| 5,365,935 A | * | 11/1994 | Righter et al. | |
| 5,458,548 A | * | 10/1995 | Crossing et al. | |
| 5,820,567 A | * | 10/1998 | Mackie | |
| 6,026,335 A | * | 2/2000 | Atlas | |

* cited by examiner

*Primary Examiner*—Scott M. Getzow
(74) *Attorney, Agent, or Firm*—Crowell & Moring LLP (57) ABSTRACT

A method and apparatus utilizes conventional wireless heart rate monitor technology by providing a person with the ability to set upper and lower heart rates, i.e. a target zone, merely by inputting his or her age. Depending upon the physical conditioning of the user, the upper and/or lower limits can be selectively changed. The user also has the capability to program a desired time accumulation goal within the target zone and to observe, both during and after the exercise period, how much time has accumulated inside the target zone.

5 Claims, 12 Drawing Sheets

| LOWER LIMIT 65% | LOWER LIMIT 65% | LOWER LIMIT 65% | LOWER LIMIT 65% |
|---|---|---|---|
| 130 | 130 | 130 | 130 |
| 129 | 129 | 129 | 129 |
| 129 | 129 | 129 | 129 |
| 128 | 128 | 128 | 128 |
| 127 | 127 | 127 | 127 |
| 127 | 127 | 127 | 127 |
| 126 | 126 | 126 | 126 |
| 125 | 125 | 125 | 125 |
| 125 | 125 | 125 | 125 |
| 124 | 124 | 124 | 124 |
| 124 | 124 | 124 | 124 |
| 123 | 123 | 123 | 123 |
| 122 | 122 | 122 | 122 |
| 122 | 122 | 122 | 122 |
| 121 | 121 | 121 | 121 |
| 120 | 120 | 120 | 120 |
| 120 | 120 | 120 | 120 |
| 119 | 119 | 119 | 119 |
| 118 | 118 | 118 | 118 |
| 118 | 118 | 118 | 118 |
| 117 | 117 | 117 | 117 |
| 116 | 116 | 116 | 116 |
| 116 | 116 | 116 | 116 |
| 115 | 115 | 115 | 115 |
| 114 | 114 | 114 | 114 |
| 114 | 114 | 114 | 114 |
| 113 | 113 | 113 | 113 |
| 112 | 112 | 112 | 112 |
| 112 | 112 | 112 | 112 |
| 111 | 111 | 111 | 111 |
| 111 | 111 | 111 | 111 |
| 110 | 110 | 110 | 110 |
| 109 | 109 | 109 | 109 |
| 109 | 109 | 109 | 109 |
| 108 | 108 | 108 | 108 |
| 107 | 107 | 107 | 107 |
| 107 | 107 | 107 | 107 |
| 106 | 106 | 106 | 106 |
| 105 | 105 | 105 | 105 |
| 105 | 105 | 105 | 105 |
| 104 | 104 | 104 | 104 |
| 103 | 103 | 103 | 103 |
| 103 | 103 | 103 | 103 |
| 102 | 102 | 102 | 102 |
| 101 | 101 | 101 | 101 |
| 101 | 101 | 101 | 101 |

SET AGE

FIG.7b

BLINKING

SET TZ ALARM

FIG.7c

BLINKING

SET TZ HIGH

FIG.7d

BLINKING

SET TZ LOW

FIG.7e

BLINKING

AGE-BASED HEART RATE TARGET ZONE METHOD AND APPARATUS

This application is a continuation of application Ser. No. 08/595,282, filed Feb. 1, 1996 now U.S. Pat. No. 6,163,718.

BACKGROUND AND SUMMARY OF THE INVENTION

The present invention relates to a heart rate monitor, and more particularly, to a heart rate monitor which can be incorporated into wrist watches, belt-clip devices and the like for allowing the user to obtain solely by inputting age data and/or to reset default high and low range settings for maintaining heart rate level, measured in beats per minute (bum), during, for example, aerobic conditioning.

Current practices and thinking involving effective aerobic conditioning hold that the appropriate heart rate level must be maintained for at least twenty minutes each workout in order to benefit the exerciser. This level or is heart rate range is also referred to as the "target zone", a range of values measured in terms of bum. One generally accepted approach for determining a person's target zone is to use the formula

MAX HEART RATE=220−AGE and then using between 50% to 90% of the maximum heart rates. Of course, this will also depend somewhat on a person's general conditioning. For example, the American Heart Association recommends that an inactive person exercise in ten to fifteen minute sessions with a lower target zone of 50% and an active person in at least thirty minute sessions with an upper target zone of 85%.

Those involved in aerobic conditioning will also be aware of alternative conventional ways for determining a target zone. Their methods include using different percentages, and adding or subtracting numbers from the maximum heart rate depending upon physical condition or other relevant criteria. Alternatively, or in addition, heart rate levels can be measured and tracked during the exercise or conditioning periods using wireless monitors.

As is also well known, such monitors measure the actual electrical ECG signals from the person's chest skin via a chest belt transmitter which transmits, for example, a signal to a wrist display via a high frequency field. The wrist display electronics receive the signals, interpret them and display the actual current bpm. Commercially available wristwatch-style heart monitors include the "Heartsafe-T" and the "2000" offered by Cardiosport USA Ltd. of Overland Park, Kans., the "Accurex", "Edge", "Pacer", "Favor", "Vantage XL" and "Cyclovantage" offered by Polar Electro Inc. of Port Washington, N. Y., and the "CARDIOCHAMP" offered by Systems Dynamics. Typically, such devices will display time-of-day, elapsed time, heart rate recording and target zone, average heart rate and so on.

Conventional wireless heart rate monitors typically require, however, that the user manually program his or her specific high and low range settings. In order to do this properly, the user must know one of the several target-zone formulas and how to calculate individual ranges or to have a chart available for obtaining the range. In either case, the range values must be then manually input.

It is an object of the present invention to provide a greatly simplified wireless heart rate setting and monitoring method and device which allows the user to obtain the appropriate target zone automatically merely by entering his or her age. The target zone, e.g. 65% to 85% of maximum heart rate, will then be calculated according to any one of a number of algorithms which can be pre-programmed and/or later programmed in the application software of a microprocessor within a device worn by the person.

An advantage of the present invention is that a target zone can be instantly calculated using a variety of formulas which can also take account of physical condition, gender, etc., but which is primarily based and completely set by the user merely by inputting his or her age.

This object and advantage has been achieved by providing a wireless heart rate monitor in the form of a display device, i.e. a display worn on the exerciser's wrist or a belt-clip device, and a wireless transmitter belt worn on the chest in proximity to the heart for transmitting electrical signals representative of heart rate to the wrist or belt display device.

BRIEF DESCRIPTION OF TBE DRAWINGS

These and other objects, features and advantages of the present invention will become more readily apparent from the following detailed description thereof when taken in conjunction with the accompanying drawings wherein.

DETAILED DESCRIPTION OF THE DRAWINGS

Figures 1, 2:
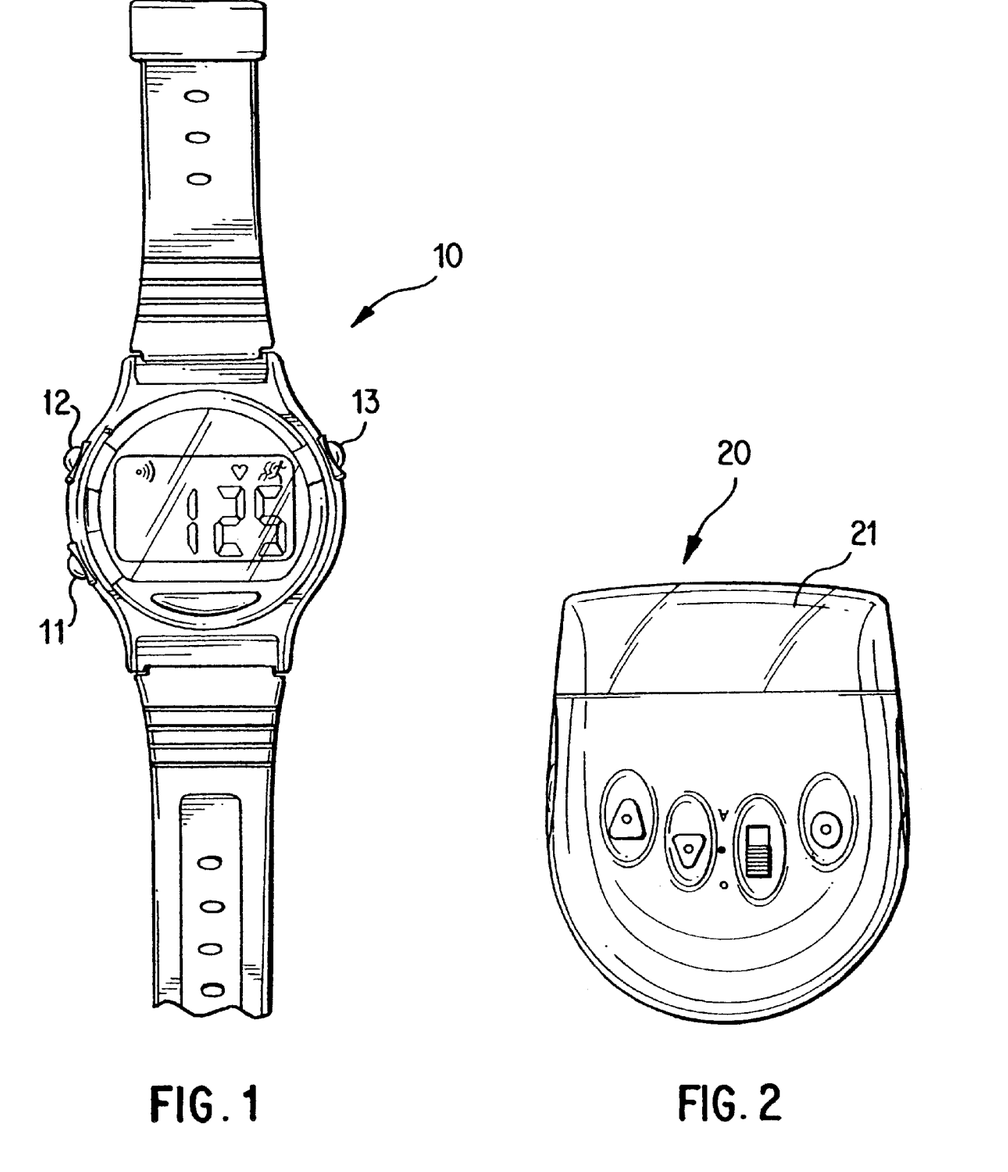
FIG. 1 is a plan view of one embodiment a wristwatch-type display device for a monitor incorporating the present invention.
FIG. 2 is a plan view of a belt-clip type display device for a monitor incorporating the present invention.
Figure 3A:
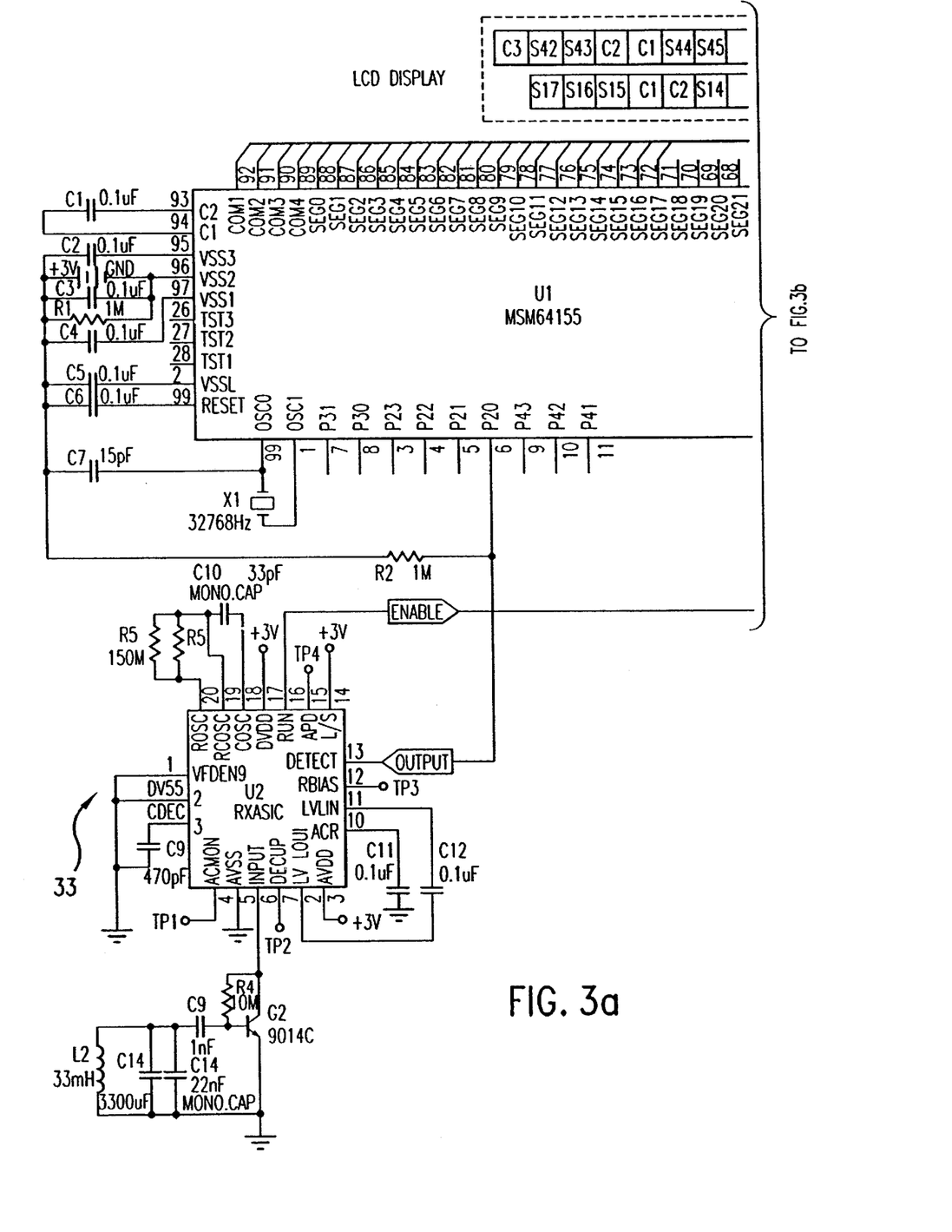
FIG. 3 is a schematic diagram of one embodiment of an electronic circuit for implementing the invention as incorporated in the devices shown in FIGS. 1 and 2.
Figure 3B:
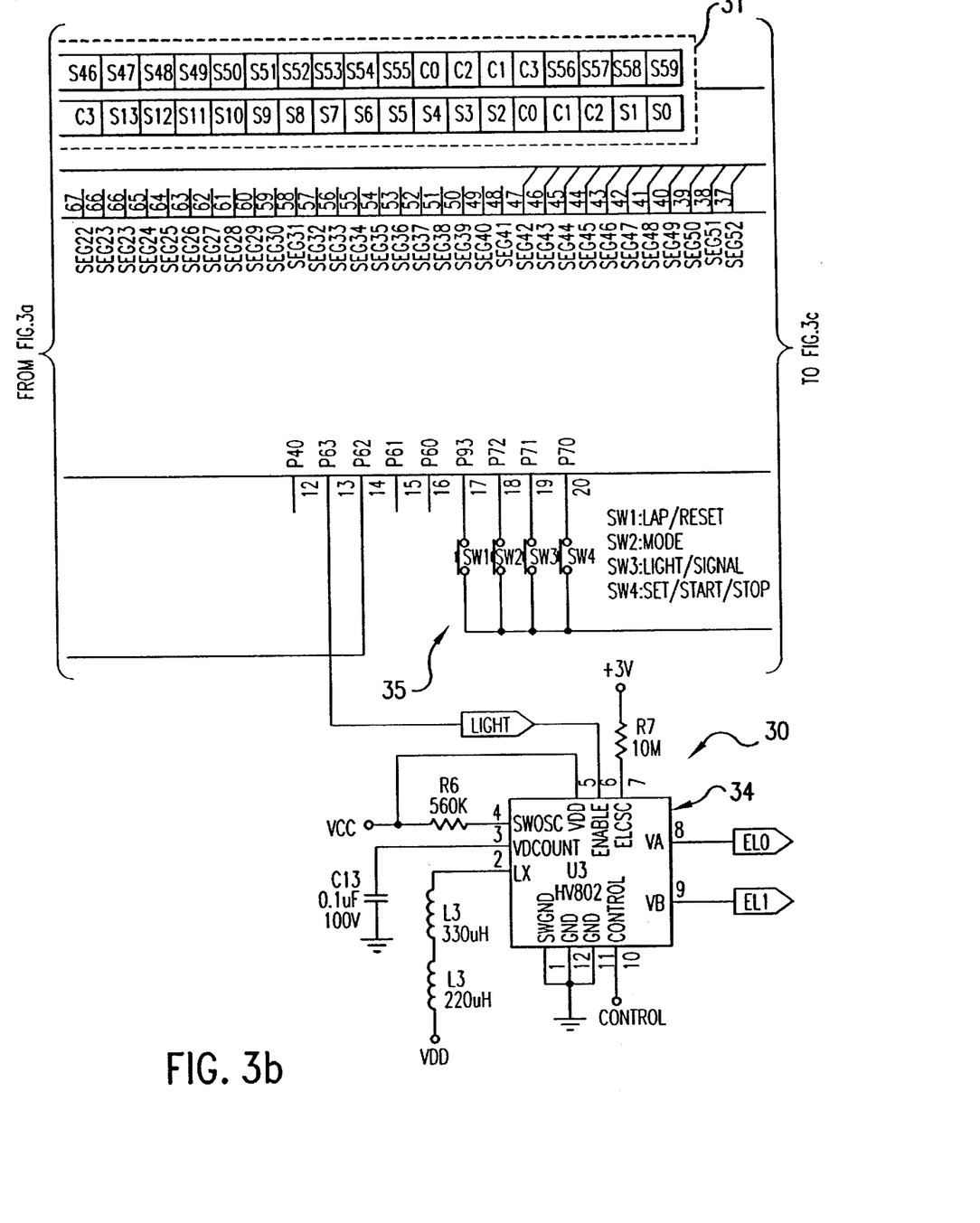
Figure 3C:
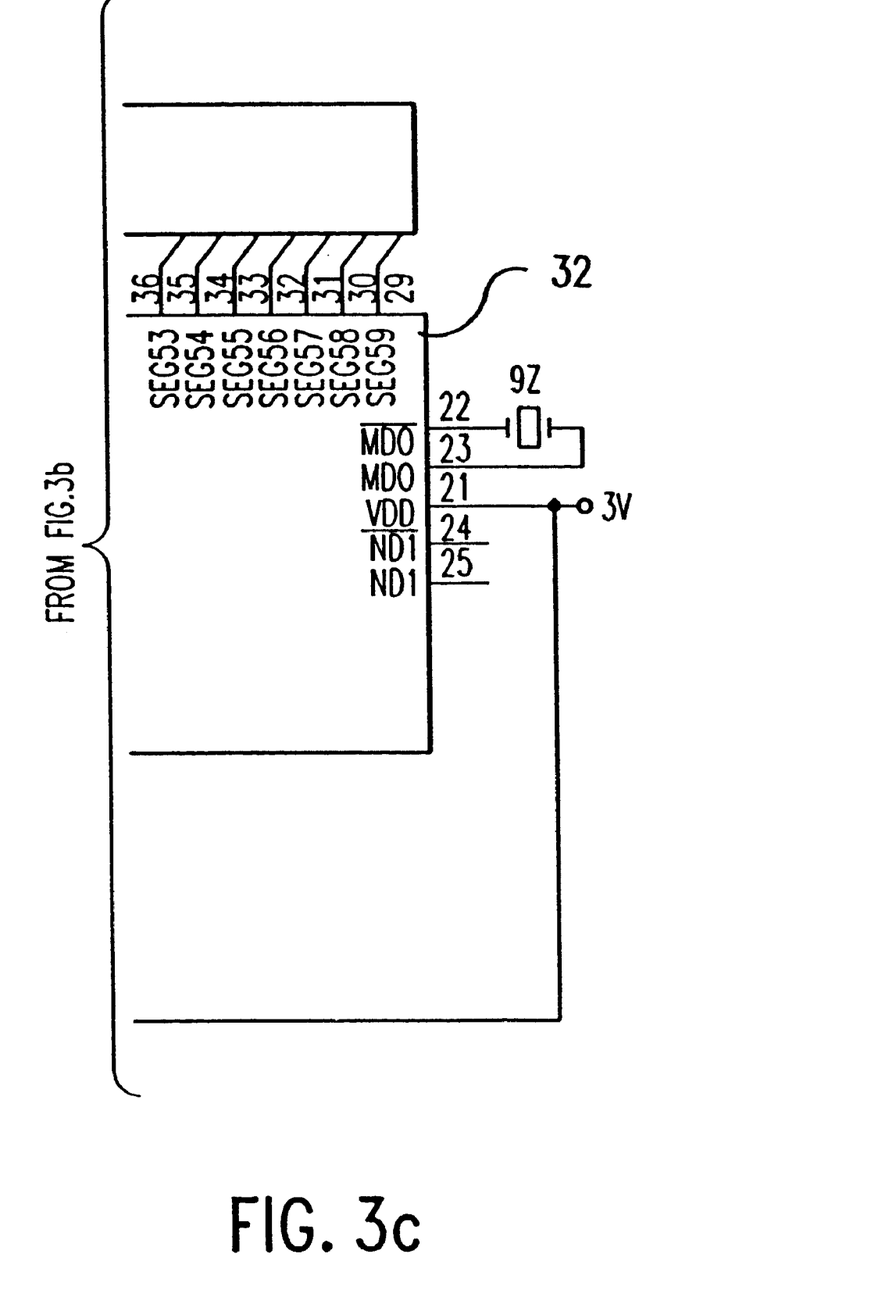

A typical wristwatch heart rate monitor designated by the numeral 10 is shown in FIG. 1 in which an exemplary heart rate of 125 bpm is currently displayed on the face 11. In the following discussion, it will be recognized, however, that the same data and operation can be integrated in a pedometer-type belt-clip monitor designated by the numeral 20 in which the user clips the monitor to his or her belt or clothes and reads the heart rate data looking downwardly into the display area 21 at the top of the monitor. In either case, the design of the electronic circuitry using conventional components and techniques will now be apparent to one skilled in the art and, for example, in one embodiment can be implemented in accordance with the circuit designated by the numeral 30 in FIG. 3 which uses an LCD display 31 electrically connected with a MPU 32 and associated circuitry such as the receiver ASIC 33 for receiving the heart rate data from the belt (not shown) via wireless transmission, a light control circuit 34 for controlling the display lighting using known EL technology, and the several switches designated generally by the numeral 35 for various functions such as the "SET" and "MODE" buttons described above.

Figure 4:
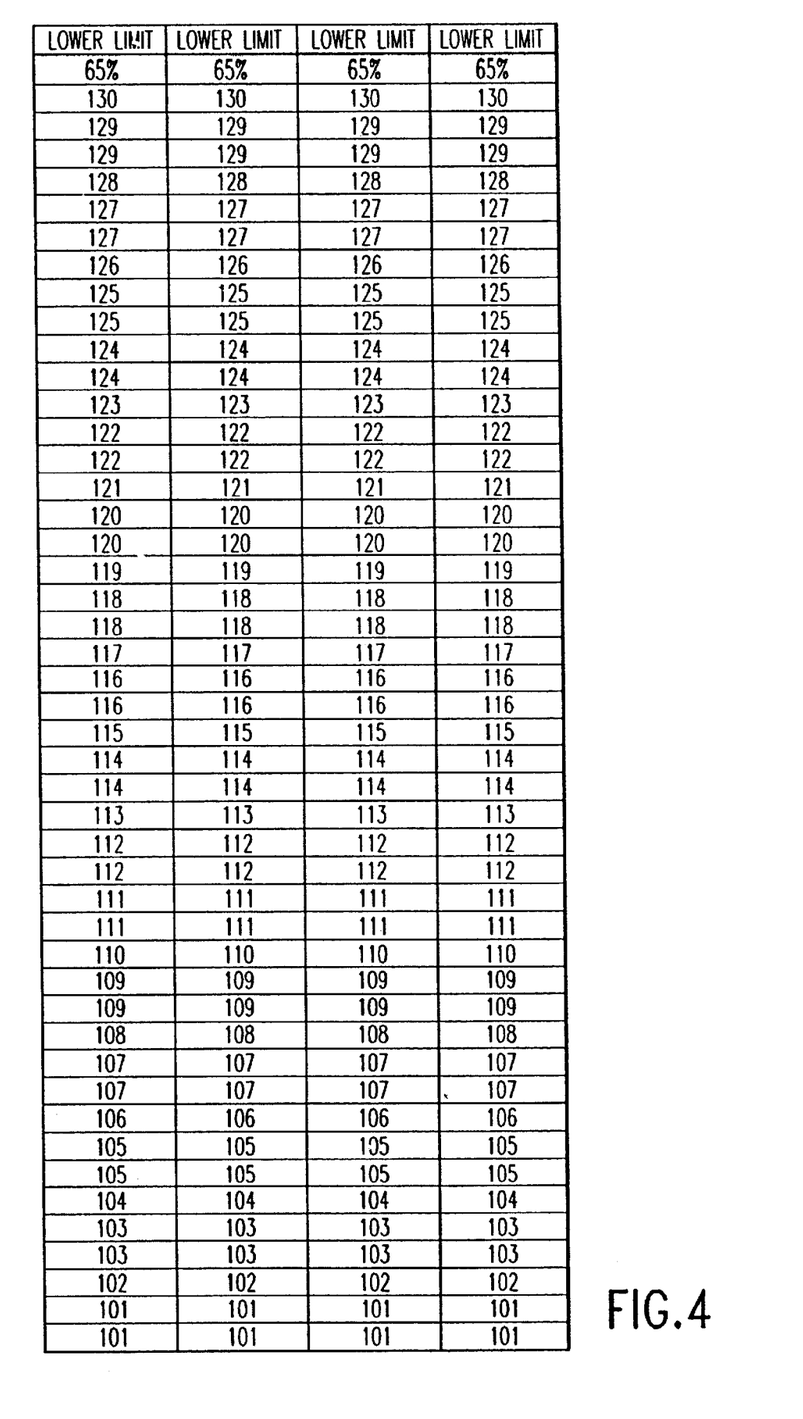
FIG. 4 is a table of upper and lower target zone limits for incorporation in the memory of the microprocessor used in the circuitry for the monitors of FIGS. 1 and 2.
Figure 5A:
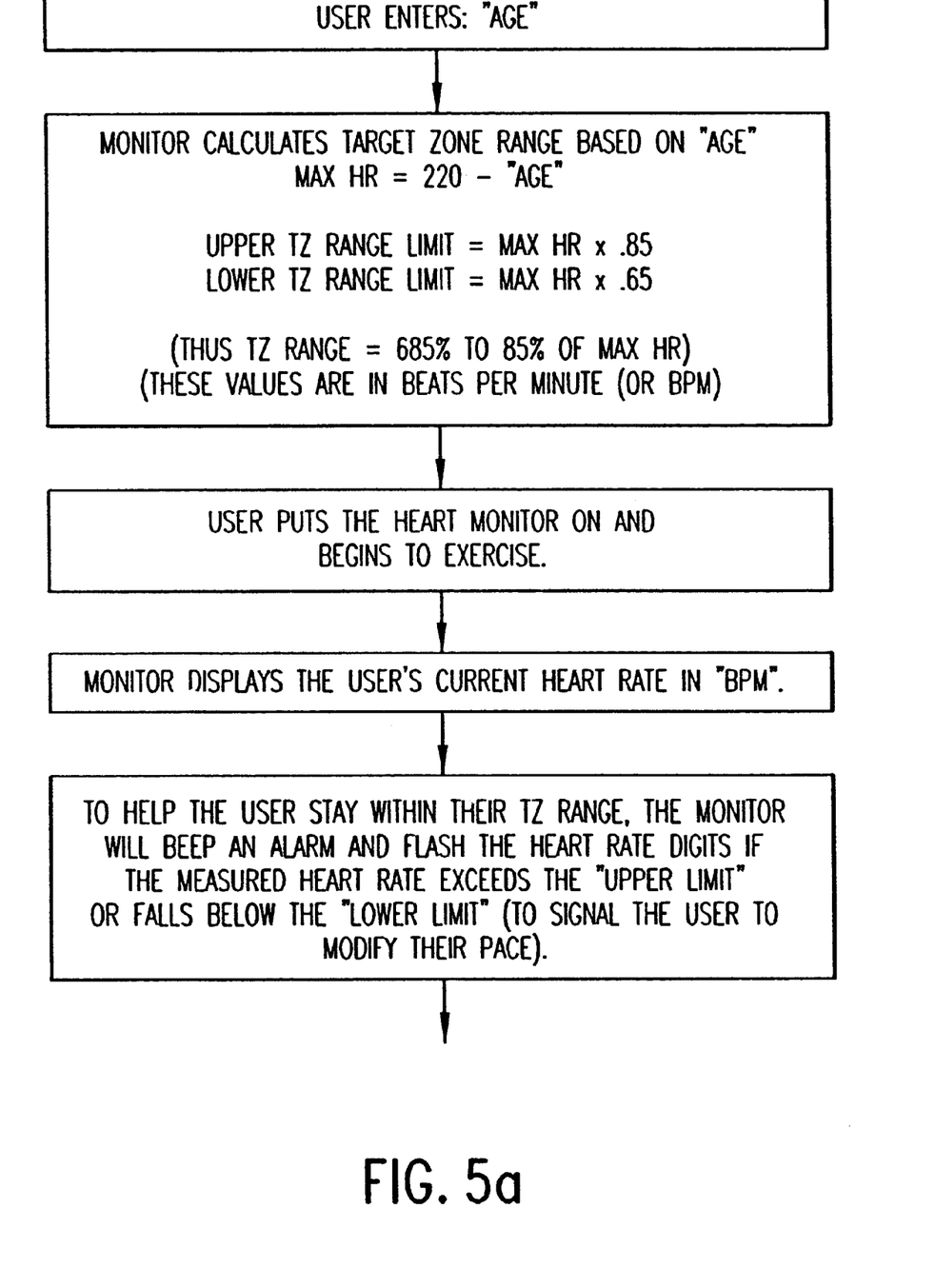
FIG. 5a is an overview flow chart of the values stored in the electronic circuitry of the monitors of FIGS. 1 and 2.
Figure 5B:
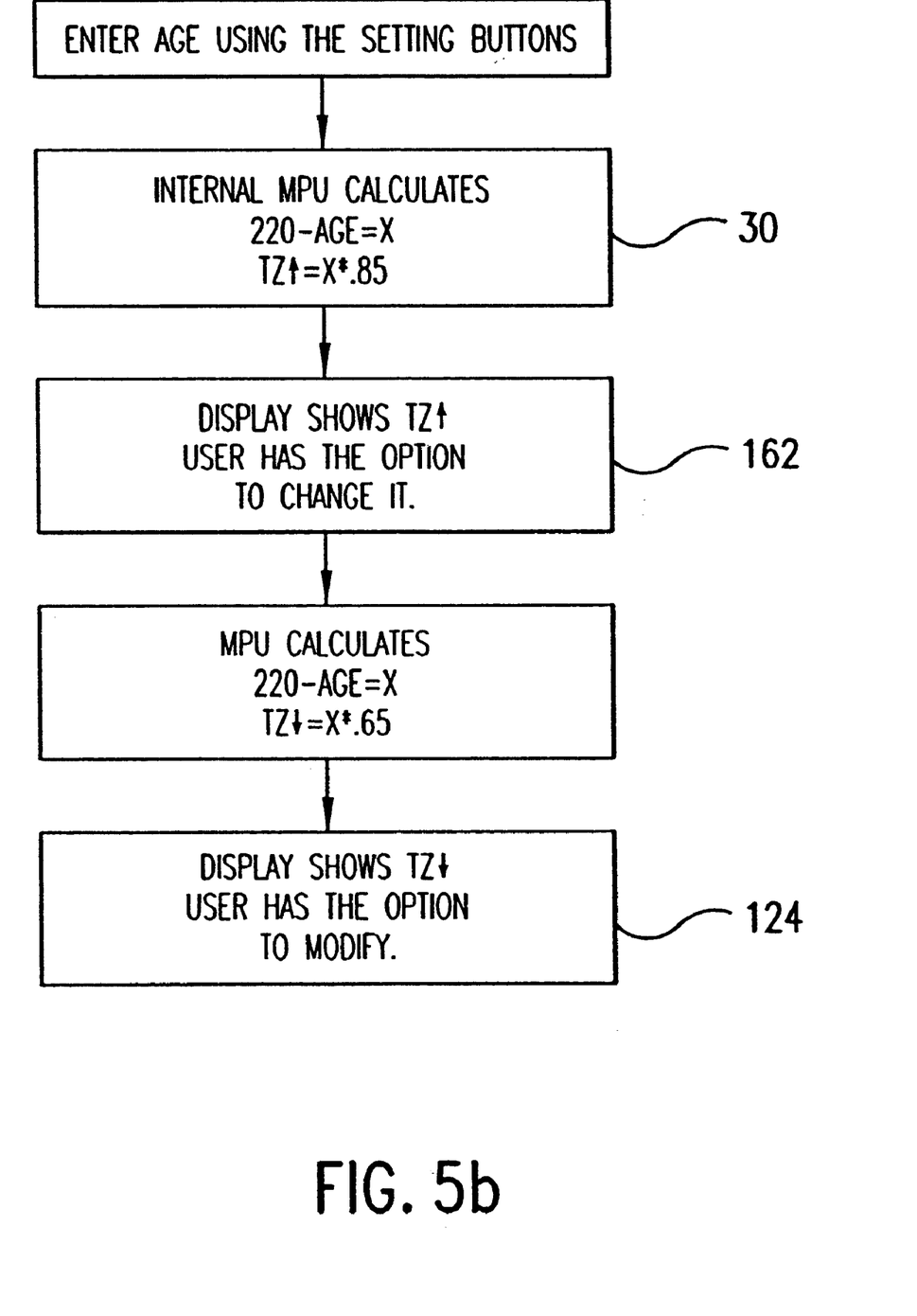
FIG. 5b is an overview flow chart similar to FIG. 5a but showing the results of inputting age 30 based upon the values obtained from the table of FIG. 4.
Figure 6:
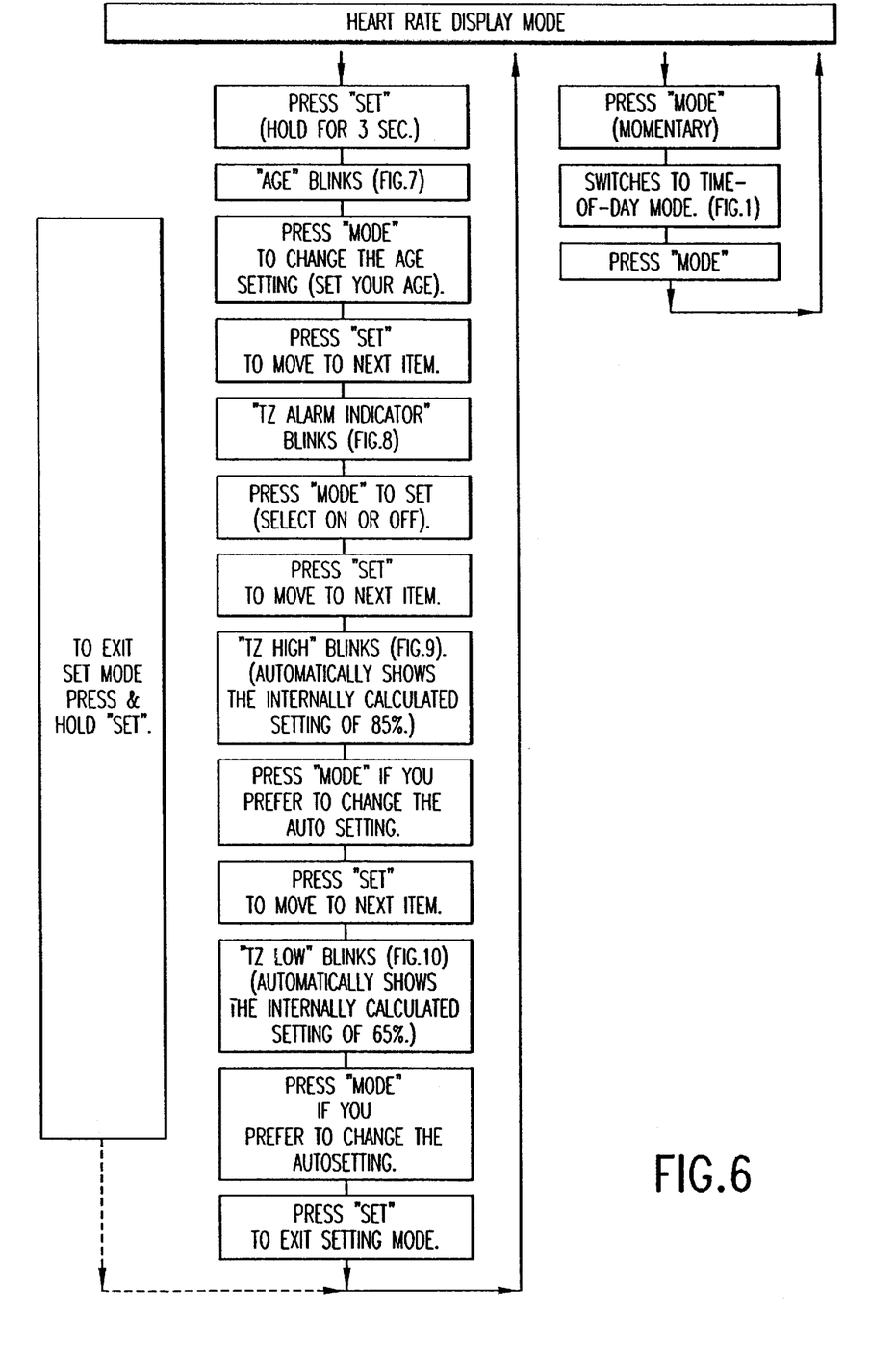
FIG. 6 is a detailed flow chart of how the age data in FIG. 4 is input and output in the monitors of FIGS. 1 and 2 beginning with the default heart rate display mode.

The data found in the table of FIG. 4 assigns a lower heart rate limit, upper heart rate limit and maximum heart rate limit for a particular set of ages, in this example ages 20 through 65. The data can be programmed into the microprocessor of a circuit of the type shown in FIG. 3. Again, it will be clearly understood that the different age ranges as well as upper and lower limits can be used depending upon the formula employed, although generally speaking there will usually not be a great deal of variation. Furthermore, the circuitry can be implemented such that the percentages of calculating the upper and lower limits can be selectively modified as, for example, the progress of the person wearing the monitor permits higher limits.

In using the monitor of either FIG. 1 or FIG. 2, the person to be monitored will, as seen in FIGS. 5a, 5b, 6 and 7a–7e, input age data using setting buttons on the monitor. The internal microprocessor in the monitor will use the table in FIG. 4, or calculate the upper heart rate limit (UTZ or TZ↑) using formulas such as 220−Age=x and UTZ=x·0.85. If the age of the person is, for example, 30, the monitor display will then display a default upper target zone of 162 bpm. As noted above, the user then can have the option to raise or lower that number depending upon other factors such as physical condition. After setting the UTZ, the microprocessor then calculates the lower heart rate limit (LTZ or TZ↓) using LTZ=x·0.65. In the above example, a default LTZ is calculated as 124 bpm, but again this can be raised or lowered before being set by the user.

Figure 7A:
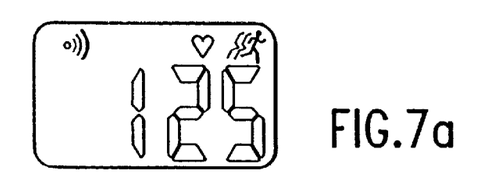
FIGS. 7a through 7e are views of the display of the monitor devices shown in FIGS. 1 and 2 in relation to the detailed flow chart of FIG. 6.
Figure 7B:
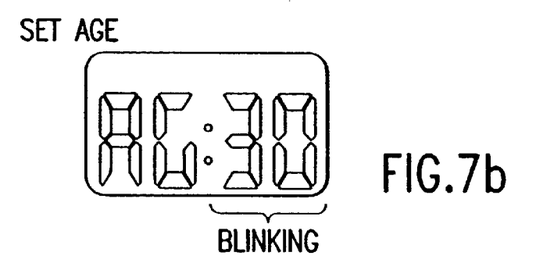
Figure 7C:
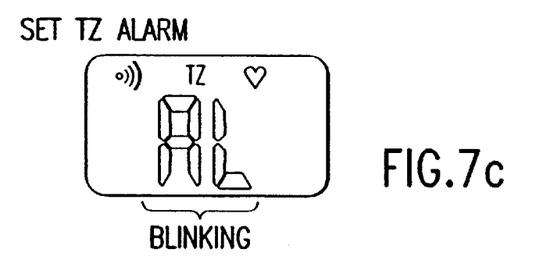
Figure 7D:
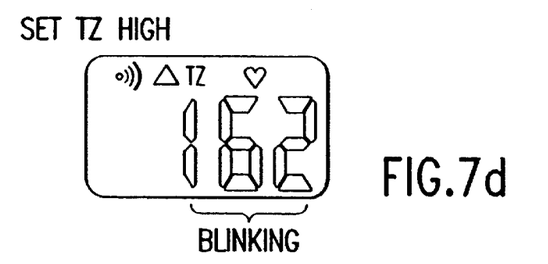

FIGS. 6 and 7(a) through 7(e) explain the foregoing operation in more detail with specific reference to how the data is displayed on the monitor display. In particular, to enter the setting mode, the "SET" button 12 (FIG. 1) is held for 3 seconds. Prior to the pressing of the SET button and assuming the transmitter is strapped to the chest, the monitor will, as a default setting, display the wearer's current heart rate, e.g. 125 bpm (FIG. 7(a)). After the expiration of 3 seconds, a default age will blink on the monitor display as seen in FIG. 7 (b). The user will then press the "MODE" button 13 to enter his or her age and then again press the "SET" button 12. Thereafter the "ITZ ALARM" indicator blinks, as seen in FIG. 7(c), and the user will press the "MODE" button 13 to select "ON" or "OFF". The default condition is "ON" in which case the alarm display is steady, whereas the "OFF" condition will blink. The "SET" button 12 is then pressed again, at which time the circuitry causes the "TZ HIGH" or upper heart rate limit calculated based upon the above formulas or selected from a stored table to be displayed. In the illustrated example, the default UTZ based upon age 30 is 162 bpm.

Figure 7E:
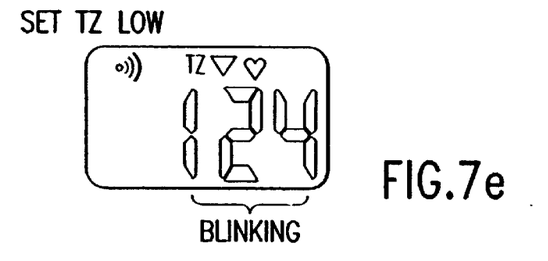

This default number blinks until the "SET" button 12 is again pressed.

If the user wishes to change the UTZ, he or she will press the "MODE" button 13 for incremental change to raise (or lower) the setting. After obtaining the desired value, the user presses the "SET" button 12 and the monitor circuitry will then display the "TZ LOW" or lower heart rate limit which the user can change in a similar manner. The user can then exit the setting mode by holding the "SET" button 12 for 3 or more seconds. Then the monitor will return to the heart rate display mode.

In addition, the user can, by momentarily pressing the "MODE" button 13 after exiting the setting mode, obtain a display of the time of day on the monitor display. By again pressing the "MODE" button 13, the circuitry will return the monitor to the heart rate display mode. During the latter mode when the user is exercising and the monitor is displaying current heart rate, the alarm will signal the user if the heart rate falls below the LTZ or exceeds the UTZ by, for example, beeping and flashing either the upper limit or the lower limit to allow the user to modify his or her pace. Once the user's heart rate returns within the range, the unit will stop beeping and flashing, and the current heart rate will be steadily displayed as seen in the example of FIG. 1. The monitor of the present invention has the advantage of allowing the user to establish a range merely by entering age.

Figure 8A:
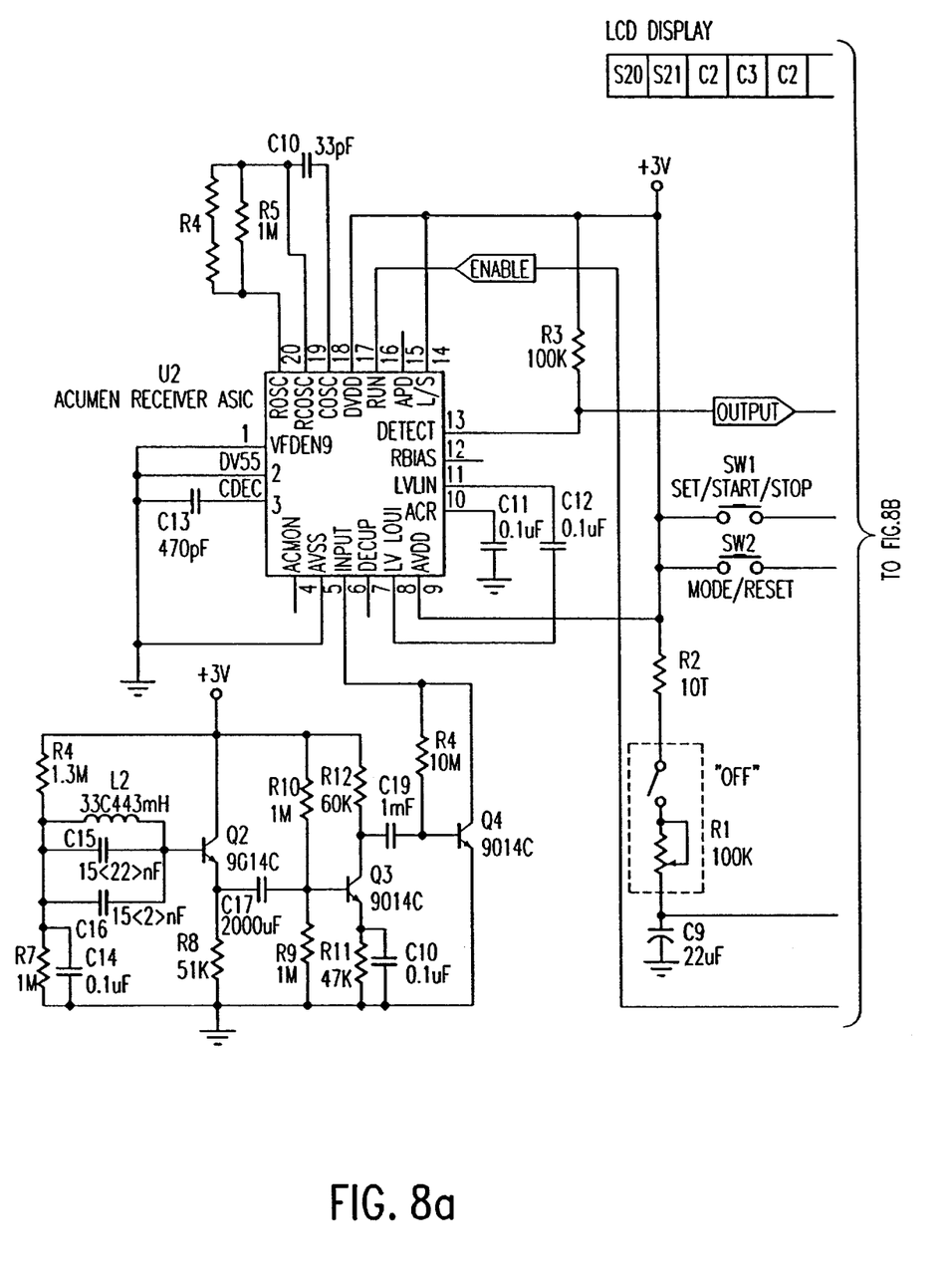
FIG. 8 is a schematic diagram of a circuit which can be incorporated in the monitor of FIG. 2 for tracking Heart Rate.
Figure 8B:
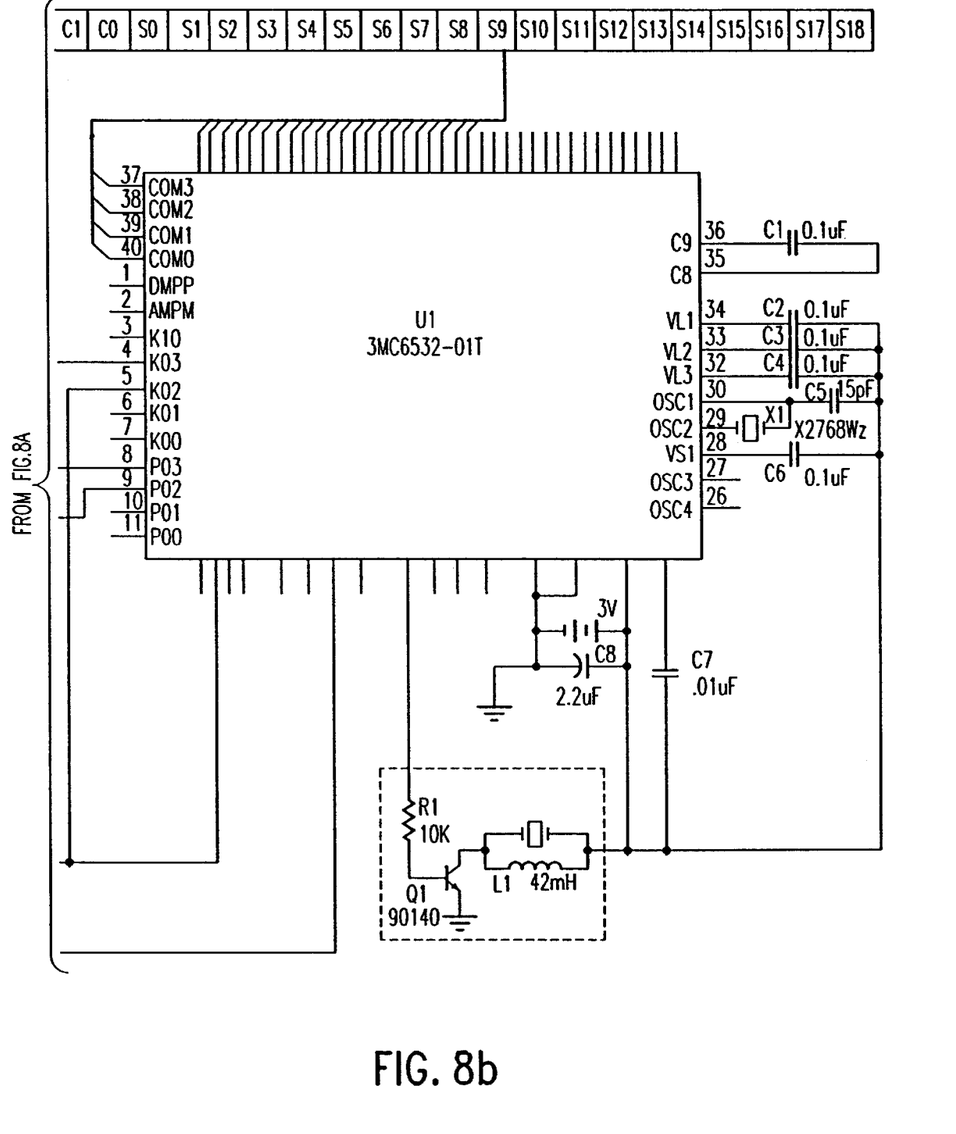
Figure 8C:
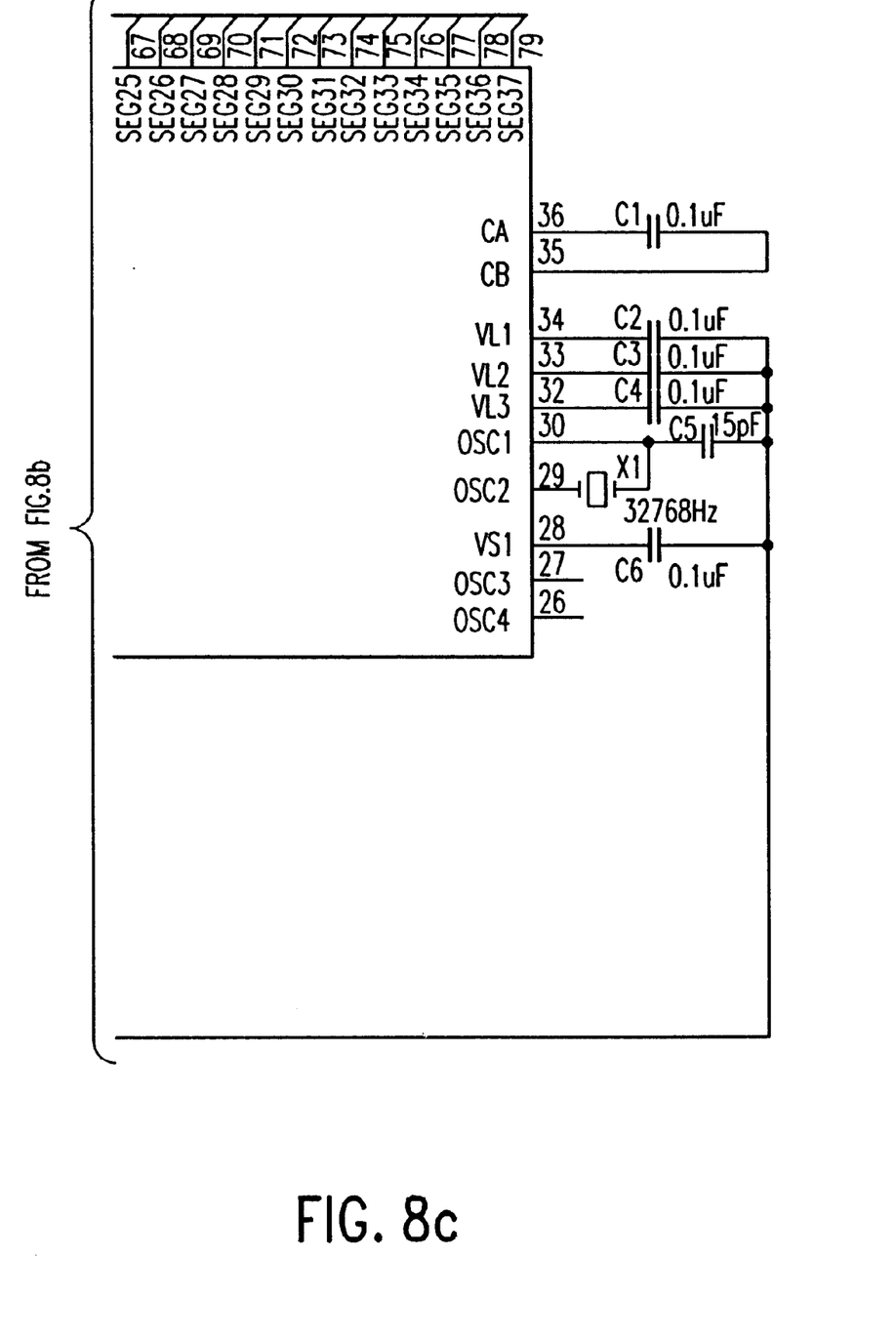

In a further modification, a heart rate monitor of the type shown in FIG. 2 can also "track" the user's heart rate. That is, with appropriate circuitry, of the type shown in FIG. 8 the monitor can also display both during and after the exercise period how much time the user's heart rate has accumulated within the target zone in contrast with current heart monitors which provide this data only after the period on a "MEMORY RECALL" mode. Moreover, the monitor of the present invention can optionally provide a desired or target "Time Accumulation Goal" so that the user can predetermine how much time he or she desires for obtaining a heart rate within the target zone. Upon achievement of the preset goal, an alarm will sound, thereby allowing the user to obtain maximum efficiency in the minimum amount of time, while avoiding harmful excessive heart rates and unbeneficial low heart rates.

The above-described method and apparatus are not strictly limited to heart monitors worn by a user. For example, the invention is also applicable for exercise machine displays, medical cardiac monitors, pedometers, pulse meters (ear clip and finger tip devices) and the like.

Although the invention has been described and illustrated in detail, it is to be clearly understood that the same is by way of illustration and example, and is not to be taken by way of limitation. The spirit and scope of the present invention are to be limited only by the terms of the appended claims.

What is claimed is:

1. A method for monitoring heart rate of a person, consisting essentially of:
   (a) inputting age of the person into a unit which is worn on the person so as to be portable;
   (b) electronically obtaining a target zone consisting of an upper limit and lower limit of the heart rate based solely on the person's age; and
   (c) issuing a signal when the heart rate is outside the target zone.

2. The method according to claim 1, further comprising the steps of:
   (d) setting a time accumulation goal for an amount of time actually incurred within the target zone; and
   (e) displaying accumulated time within the target zone during a monitoring period.

3. A portable apparatus for monitoring heart rate of a person, comprising:
   means for attaching the apparatus to the person;
   means for measuring a heart rate of a person during a monitoring period; and
   means for displaying the measured heart rate consisting of electronic circuitry for setting a target zone having an upper heart rate limit and a lower heart rate limit based solely upon inputted age of the person.

4. The apparatus according to claim 3, wherein the displaying means is configured to allow the person to set a time accumulation goal for an amount of time actually incurred within the target zone and to display accumulated time within the target zone during the monitoring period.

5. The apparatus according to claim 3, wherein the measuring means and the displaying means are operatively connected via a wireless transmission means.

* * * * *

UNITED STATES PATENT AND TRADEMARK OFFICE
CERTIFICATE OF CORRECTION

PATENT NO.        : 6,345,197 B1
APPLICATION NO.   : 09/665171
DATED             : February 5, 2002
INVENTOR(S)       : Robert A. Fabrizio It is certified that error appears in the above-identified patent and that said Letters Patent is hereby corrected as shown below:

Fig. 4 should be replaced with the attached replacement sheet.

Signed and Sealed this

Twenty-ninth Day of July, 2008

JON W. DUDAS
*Director of the United States Patent and Trademark Office*

|  | Lower limit | Upper limit | Max HR |
|---|---|---|---|
| AGE | 65% | 85% | 100% |
| 20 | 130 | 170 | 200 |
| 21 | 129 | 169 | 199 |
| 22 | 129 | 168 | 198 |
| 23 | 128 | 167 | 197 |
| 24 | 127 | 167 | 196 |
| 25 | 127 | 166 | 195 |
| 26 | 126 | 165 | 194 |
| 27 | 125 | 164 | 193 |
| 28 | 125 | 163 | 192 |
| 29 | 124 | 162 | 191 |
| 30 | 124 | 162 | 190 |
| 31 | 123 | 161 | 189 |
| 32 | 122 | 160 | 188 |
| 33 | 122 | 159 | 187 |
| 34 | 121 | 158 | 186 |
| 35 | 120 | 157 | 185 |
| 36 | 120 | 156 | 184 |
| 37 | 119 | 156 | 183 |
| 38 | 118 | 155 | 182 |
| 39 | 118 | 154 | 181 |
| 40 | 117 | 153 | 180 |
| 41 | 116 | 152 | 179 |
| 42 | 116 | 151 | 178 |
| 43 | 115 | 150 | 177 |
| 44 | 114 | 150 | 176 |
| 45 | 114 | 149 | 175 |
| 46 | 113 | 148 | 174 |
| 47 | 112 | 147 | 173 |
| 48 | 112 | 146 | 172 |
| 49 | 111 | 145 | 171 |
| 50 | 111 | 145 | 170 |
| 51 | 110 | 144 | 169 |
| 52 | 109 | 143 | 168 |
| 53 | 109 | 142 | 167 |
| 54 | 108 | 141 | 166 |
| 55 | 107 | 140 | 165 |
| 56 | 107 | 139 | 164 |
| 57 | 106 | 139 | 163 |
| 58 | 105 | 138 | 162 |
| 59 | 105 | 137 | 161 |
| 60 | 104 | 136 | 160 |
| 61 | 103 | 135 | 159 |
| 62 | 103 | 134 | 158 |
| 63 | 102 | 133 | 157 |
| 64 | 101 | 133 | 156 |
| 65 | 101 | 132 | 155 |

Fig.4